(12) United States Patent
Stamm et al.

(10) Patent No.: US 6,683,204 B1
(45) Date of Patent: Jan. 27, 2004

(54) METHOD FOR PRODUCING MONOISOCYANATES AND OLIGOISOCYANATES

(75) Inventors: Armin Stamm, Mainz (DE); Heinz-Josef Kneuper, Niederkirchen (DE); Lucien Thil, Limburgerhof (DE); Jochem Henkelmann, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 113 days.

(21) Appl. No.: 10/070,393

(22) PCT Filed: Aug. 23, 2000

(86) PCT No.: PCT/EP00/08221

§ 371 (c)(1),
(2), (4) Date: Mar. 4, 2000

(87) PCT Pub. No.: WO01/17951

PCT Pub. Date: Mar. 15, 2001

(30) Foreign Application Priority Data

Sep. 4, 1999 (DE) .......................... 199 42 299

(51) Int. Cl.⁷ .......................................... C07C 263/10
(52) U.S. Cl. ..................................... 560/347
(58) Field of Search ......................... 560/347

(56) References Cited

U.S. PATENT DOCUMENTS

| 3,371,114 A | 2/1968 | Sayigh ............... 260/545 |
|---|---|---|
| 3,440,268 A | 4/1969 | Stamm ............... 260/453 |
| 3,484,466 A | 12/1969 | Sayigh ............... 260/397 |
| 3,492,331 A | 1/1970 | Sayigh ............... 260/453 |
| 4,379,769 A | 4/1983 | Levitt ............... 260/545 |
| 5,925,783 A | 7/1999 | Jost et al. ............... 560/347 |

FOREIGN PATENT DOCUMENTS

| EP | 021641 | 1/1981 |
|---|---|---|
| GB | 1114085 | 5/1968 |
| GB | 1359428 | 7/1974 |
| WO | 96/06826 | 3/1996 |

OTHER PUBLICATIONS

Findeisen et al., *Methoden d. org. Chemie*, 4(E4), pp. 741–751, 1983.

Primary Examiner—Michael L. Shippen
(74) Attorney, Agent, or Firm—Keil & Weinkauf

(57) ABSTRACT

The present invention relates to a process for the preparation of aliphatic, cycloaliphatic, araliphatic and aromatic mono- and oligoisocyanates by phosgenation of the corresponding primary amines at atmospheric pressure, which comprises a) introducing a catalytic amount of a monoisocyanate (isocyanate a) into an inert solvent together with phosgene;

b) adding the primary amine, and c) reacting the resulting reaction mixture with phosgene.

7 Claims, No Drawings

METHOD FOR PRODUCING MONOISOCYANATES AND OLIGOISOCYANATES

The invention relates to a process for the preparation of mono- and oligoisocyanates by reacting primary amines with phosgene in the presence of a catalyst.

Isocyanates are industrial products which have a large number of uses in the field of polyurethane plastics. However, certain isocyanates are also used in the preparation of pharmaceutical active ingredients.

The synthesis of isocyanates by reacting amines with phosgene has been known for some time. In principal, two processes are described in the literature, one of which is carried out at atmospheric pressure and the other is carried out at increased pressure. Phosgenation under increased pressure is disadvantageous since it requires much more complex industrial apparatus to control the increased safety risk, the release of phosgene.

For sulfonyl isocyanates, U.S. Pat. No. 3,371,114 and U.S. Pat. No. 3,484,466 disclose a preparation process at atmospheric pressure in which a solution of a sulfonylamide and an isocyanate as catalyst in an inert solvent is reacted with phosgene. In the process, the corresponding sulfonylurea is formed as an intermediate, which reacts with phosgene to give the desired sulfonyl isocyanate.

Alkyl and aryl isocyanates are usually prepared by the phosgenation process, described, for example, in Houben-Weyl, Methoden der organischen Chemie [Methods in Organic Chemistry], 4th Edition, Volume E4, pages 741–751, Georg Thieme Verlag Stuttgart, 1983, from the corresponding amines in two phases at atmospheric pressure. In the first phase, the cold phosgenation, the amine is reacted with an excess of phosgene in very dilute solution and at low temperatures to give the corresponding carbamyl chloride, from which, in the second phase at elevated temperature, the hot phosgenation, the isocyanate forms. Aliphatic and cycloaliphatic primary amines are more difficult to phosgenate because of their increased basicity compared with aromatic amines, and lead to an increased formation of byproducts. A disadvantage of these processes is, in addition to the fact that the phosgenation is carried out in two phases, the formation of an intermediate solids suspension of sparingly soluble carbamyl chloride and amine hydrochloride, which in turn renders an increased dilution of the reaction medium necessary in order to prevent deposits and blockages of parts of the equipment. Because of the accumulation of solids which occurs, this process cannot be carried out continuously at atmospheric pressure. Furthermore, symmetrically N,N'-substituted urea forms as a byproduct, the formation of which can only be suppressed at the expense of drastically reduced space-time yields.

Aliphatic and cycloaliphatic amines are frequently used in the form of their salts in the cold/hot phosgenation. However, these salts are sparingly soluble in the reaction medium, meaning that additional reaction stages and very long reaction times are necessary.

Furthermore, it is known from GB 1 114 085, U.S. Pat. No. 3,492,331 and H. Ulrich, Chemistry & Technology of Isocyanates, Wiley & Sons, 1996, pages 328–330, to optimize the reaction of primary amines with phosgene by the addition of catalysts such as dimethylformamide, phenyltetramethylguanidine, 2,4,6-trimethylpyridine or carbodiimidazole. Some of these catalysts must be used in equimolar amounts and form sparingly soluble salts under the reaction conditions.

It is an object of the present invention to provide a process, which can be used for aliphatic, cycloaliphatic, araliphatic and aromatic primary amines, for the preparation of the corresponding mono- and oligoisocyanates using phosgene which can be carried out either continuously or batchwise at atmospheric pressure, does not have the above disadvantages and provides the corresponding mono- and oligoisocyanates in good yields and high selectivities.

We have found that this object is achieved by a process for the preparation of aliphatic, cycloaliphatic, araliphatic and aromatic mono- and oligoisocyanates by phosgenation of the corresponding primary amines at atmospheric pressure, in which a) a catalytic amount of a monoisocyanate (isocyanate a) is introduced into an inert solvent together with phosgene, b) the primary amine is added, and c) the resulting reaction mixture is reacted with phosgene.

The net equation underlying the process is given in scheme 1 below.

Scheme 1:

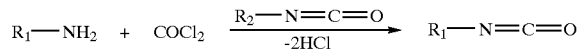

The process according to the invention has the advantage that it can be used for a large number of amines. The phosgenation is carried out according to the invention, while avoiding a division into cold and hot phosgenation, in a narrow temperature interval and at atmospheric pressure, the intermediate formation of sparingly soluble suspensions being avoided. The desired isocyanate is formed in the process, with complete conversion of the amine, in high yields and high selectivity in significantly shortened reaction times without symmetrically substituted N,N'-urea being formed from the amine as a byproduct. Since the formation of urea from the amine is not observed, it is possible by means of the process according to the invention to significantly increase the concentration of the amine in the reaction solution and thus the space-time yields. In addition, it is advantageous that the process according to the invention can be carried out either batchwise or continuously since there is no accumulation of solids.

The process according to the invention gives aliphatic, cycloaliphatic, araliphatic and aromatic mono- and oligoisocyanates of the formula I

The radical $R_1$ in formula I corresponds to the radical $R_1$ in formula IV of the amines used in the process according to the invention, which are discussed later and to which reference is made here. Preference is given to preparing mono- and diisocyanates by the process of the invention. Of lesser importance in practice, but preparable in principle are isocyanates having 3 and more isocyanate groups.

The sole catalyst used is a monoisocyanate of the formula II (isocyanate a)

or mixtures thereof, in which $R_2$ is aliphatic, cycloaliphatic, aromatic or araliphatic radicals. These can be substituted by heteroatoms, or their carbon chains can be interrupted by heteroatoms, such as oxygen and sulfur. The radical $R_2$ must, however, be inert toward phosgene, thus excluding radicals which carry NH, OH and SH groups. The aliphatic radicals can be arbitrarily branched or unbranched, saturated or unsaturated. They contain 3 to 30 carbon atoms, preferably 3 to 10 carbon atoms. Examples of aliphatic radicals are methyl, ethyl, propyl, n-butyl, isobutyl and sec-butyl.

Suitable cycloaliphatic radicals are those which have 3 to 20 carbon atoms, preferably 3 to 10 carbon atoms, such as, for example, cyclopentyl and cyclohexyl.

The aromatic radicals can be unsubstituted or arbitrarily substituted by alkyl or aryl substituents or heteroatoms. Preference is given to the aromatic radicals which are mono- or disubstituted. Examples of aromatic radicals are phenyl, chlorophenyl, o-, m- and p-tolyl.

Suitable araliphatic radicals are radicals having 7 to 12 carbon atoms, such as, for example, benzyl, although preference is given to a radical of the formula III

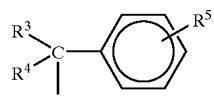

(III), in which $R_3$ and $R_4$ can be identical or different and can be hydrogen or an aliphatic, cycloaliphatic, araliphatic or aromatic radical, in which case these may be substituted by heteroatoms, or their carbon chains can be interrupted by heteroatoms, such as oxygen and sulfur. The radicals $R_3$ and $R_4$ must, however, be inert toward phosgene, thus excluding radicals carrying NH, OH and SH groups. The aliphatic radicals can be arbitrarily branched or unbranched, saturated or unsaturated. They contain 1 to 30 carbon atoms, preferably 1 to 10 carbon atoms. Examples of aliphatic radicals are methyl, ethyl, propyl, n-butyl, isobutyl and sec-butyl.

Suitable cycloaliphatic radicals are those which have 3 to 20 carbon atoms, preferably 3 to 10 carbon atoms, such as, for example, cyclopentyl and cyclohexyl.

The aromatic radicals can be unsubstituted or arbitrarily substituted by alkyl or aryl substituents or heteroatoms. Preference is given to the aromatic radicals which are mono- or disubstituted. Examples of aromatic radicals are phenyl, chlorophenyl, o-, m- and p-tolyl. $R^5$ is fluorine, chlorine, bromine or a $C_1$- to $C_4$-alkyl chain which may optionally be interrupted by a heteroatom, for example oxygen or sulfur. Preference is given to the monoisocyanate (isocyanate a), a linear aliphatic alkyl isocyanate, particularly preferably a linear aliphatic alkyl isocyanate having 3 to 10 carbon atoms, where the alkyl chain may optionally be branched, particularly preferably n-butyl isocyanate. In the case of the preparation of monoisocyanates by the process according to the invention, it is also possible to use the monoisocyanate desired as product in catalytic amounts as isocyanate a. It is, however, preferable to use an isocyanate a which is not identical to the product (isocyanate of the formula (I)) as catalyst.

The isocyanate a is generally used in a catalytic amount of from 0.01 to 25 mol %, preferably 0.5 to 20 mol %, particularly preferably 1 to 15 mol %, based on the amine.

In step a) of the process according to the invention, the isocyanate a is introduced into a solvent which is inert toward phosgene. Preferred solvents are hydrocarbons. Particular preference is given to mono- or polysubstituted aromatic hydrocarbons, such as toluene, o-, m- or p-xylene, ethylbenzene, chlorobenzene or 1,2-, 1,3- or 1,4-dichlorobenzene or mixtures thereof. Particular preference is given to xylenes, chlorobenzene and dichlorobenzenes as solvent.

The process according to the invention is carried out at atmospheric pressure and generally at a reaction temperature, which is largely constant over the three steps of the process a), b) and c), of from 20 to 200° C., preferably from 20 to 150° C., particularly preferably from 50 to 120° C.

The monoisocyanate (isocyanate a) dissolved in the inert solvent is, in step a) of the process according to the invention, heated to the reaction temperature and mixed with an excess of phosgene, based on the monoisocyanate. The molar ratio between phosgene and isocyanate a is preferably 100:1 to 5:1. Particular preference is given to using phosgene in an excess of 20:1 to 5:1, based on isocyanate a.

The phosgene can be used in the process according to the invention in steps a) and c) in gaseous form or in condensed form, preference being given to introducing the phosgene in gaseous form.

In the process according to the invention, suitable primary amines are amines of the formula IV

(IV)

which are obtainable by methods known from the literature or as a commercially available product.

$R_1$ stands for aliphatic, cycloaliphatic, aromatic or araliphatic radicals. These can be substituted by heteroatoms, or their carbon chains can be interrupted by heteroatoms, such as oxygen and sulfur. Radicals which contain OH and SH groups are excluded. Substitution by amino groups, on the other hand, is possible and leads to di- or oligoisocyanates, preference being given to diisocyanates. The aliphatic radicals can be arbitrarily branched or unbranched, saturated or unsaturated. They contain 3 to 30 carbon atoms, preferably 3 to 10 carbon atoms. Examples of aliphatic radicals are propyl, butyl, pentyl and hexyl. Suitable cycloaliphatic radicals are those having 3 to 20 carbon atoms, preferably those having 3 to 10 carbon atoms, such as cyclopentyl and cyclohexyl.

The aromatic radicals can have 4 to 10 carbon atoms, can be heteroaromatic radicals, and unsubstituted or arbitrarily substituted by alkyl or aryl substituents or heteroatoms. The aromatic radicals are preferably mono- or disubstituted. Examples of aromatic radicals are phenyl and chlorophenyl, o-, m-, p-tolyl, furfuryl, thiophenyl and pyrrolyl.

Suitable araliphatic radicals are radicals having 7 to 12 carbon atoms, such as, for example, benzyl, although preference is given to a radical of the formula V

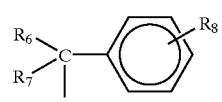

(V), in which $R_6$ and $R_7$ can be identical or different and can be hydrogen or an aliphatic, cycloaliphatic or aromatic radical, in which case these can be substituted by heteroatoms, or their carbon chains can be interrupted by heteroatoms, such as oxygen and sulfur. The radicals $R_6$ and $R_7$ must, however, be inert toward phosgene, meaning that radicals carrying NH, OH and SH groups are excluded. The aliphatic radicals can be arbitrarily branched or unbranched, saturated or unsaturated. They contain 1 to 30 carbon atoms, preferably 1 to 10 carbon atoms. Examples of aliphatic radicals are methyl, ethyl, propyl, n-butyl, isobutyl and sec-butyl.

Suitable cycloaliphatic radicals are those which have 3 to 20 carbon atoms, preferably 3 to 10 carbon atoms such as, for example, cyclopentyl and cyclohexyl.

The aromatic radicals can be unsubstituted or arbitrarily substituted by alkyl or aryl substituents or heteroatoms.

Preference is given to the aromatic radicals which are mono- or disubstituted. Examples of aromatic radicals are phenyl, chlorophenyl, o-, m- and p-tolyl. $R_8$ is a halogen atom (F, Cl, Br) or a $C_1$- to $C_4$-alkyl chain, which may optionally be interrupted by a heteroatom, for example oxygen or sulfur. Primary amines of the formula IV which can be used are also amines in enantiomerically pure, optically active form or mixtures of the enantiomers. The process according to the invention advantageously leads during the reaction and the work-up to only a low degree of racemization, which is generally below 2%.

In the process according to the invention, preference is given to using cycloaliphatic, araliphatic and aromatic amines, in particular those which are further processed in industrial processes, such as, for example, hexamethylenediamines, cyclohexylamine, isophoronediamine, toluylenediamine, aniline, and optically active amines, such as, for example, R-(+)- and S-(−)-phenylethylamine.

In step b) of the process according to the invention, the primary amine is added to the solution of the monoisocyanate (isocyanate a), saturated with phosgene, preferably in an inert solvent. This can be carried out, for example, in the presence of a stream of inert gas, for example nitrogen. Preferred solvents are the solvents used in step a) of the process according to the invention. Particular preference is given to using the same solvent as in step a). The resulting reaction mixture is then reacted with phosgene in step c) of the process according to the invention.

The molar ratio between primary amine and the total amount of the amount of phosgene introduced in steps a) and c) is 1:10 to 1:1, particular preference being given to introducing phosgene in an amount of from 120 to 180 mol %, based on the amine.

The process according to the invention can in principle be carried out both continuously and batchwise, preference being given to a continuous operation. The process can be carried out in any desired apparatus which is suitable for a reaction with phosgene. For example, a phosgenation apparatus is used which comprises an attached carbonic acid condenser or a downstream battery of high-efficiency condensers for the condensation of phosgene.

For the preferred continuous procedure, a phosgenation apparatus is used which comprises a main reactor and after-reactor, a stripping column and, connected downstream therefrom, a condenser. In the case of the continuous procedure, a mixture of the desired isocyanate of the formula I, the catalytic amounts of the isocyanate of the formula II (isocyanate a) and phosgene in the inert solvent is preferably initially introduced.

After an after-reaction, excess phosgene and solvent are generally stripped out at temperatures from 30 to 80° C., preferably 40° C. to 60° C., condensed in the condenser and returned together to the after-reactor.

The reaction product is worked up using methods known to the person skilled in the art. Preferably, the desired isocyanate of the formula I is isolated by fractional distillation. The isocyanate a used as catalyst is preferably recovered by distillation and can be reused for further batches. The desired mono- and oligoisocyanates can be obtained in the process in yields of generally 60 to 95%, based on the primary amine used.

The examples below illustrate the invention further.

Example 1

R-(+)-Phenylethyl Isocyanate 500 g of chlorobenzene and 4.8 g of n-butyl isocyanate (0.1 mol) were introduced into a phosgenation apparatus with a downstream battery of high-efficiency condensers. A total of 50 g of phosgene was passed in at room temperature over the course of 60 minutes. The batch was then heated to 72° C., and the phosgene refluxed vigorously. At 72–82° C., a total of 121 g (1 mol) of R-(+)-phenylethylamine, dissolved in 200 g of chlorobenzene, was added dropwise over the course of 2 h, and 100 g of phosgene were introduced simultaneously. After an after-reaction time of 3 h at 80–85° C., excess phosgene was stripped out with nitrogen at 40° C. The crude product contained, according to gas chromatographic determination, 86% of R-(+)-phenylethyl isocyanate (excluding solvent) and was fractionally distilled. At 0.5 mbar and 63° C., 122.1 g of R-(+)-phenylethyl isocyanate were isolated (83% of theory).

Example 2

R-(+)-Phenylethyl Isocyanate 2.4 g of n-butyl isocyanate (0.05 mol) were introduced into 400 g of chlorobenzene in a phosgenation apparatus with a downstream battery of high-efficiency condensers. A total of 50 g of phosgene was passed in at room temperature. The batch was then heated to 79°C, and the phosgene refluxed vigorously. At 79–82° C., a total of 121 g (1 mol) of R-(+)-phenylethylamine, dissolved in 200 g of chlorobenzene, was added dropwise over the course of 1 h 40 minutes, and 100 g of phosgene were introduced simultaneously. After an after-reaction time of 3.5 h at 82–87° C., excess phosgene was stripped out with nitrogen at 40° C. The crude product contained, according to gas chromatographic determination, 89% of R-(+)-phenylethyl isocyanate (excluding solvent). 121 g of R-(+)-phenylethyl isocyanate were isolated by fractional distillation at 0.4 mbar and 66° C. (82% of theory).

Example 3

Continuous Procedure

The phosgenation apparatus used comprised a main reactor, an after-reactor, a stripping column and a downstream battery of high-efficiency condensers.

Over the course of 12 h, 164.7 g/h (corresponding to 0.26 mol/h of R-(+)-phenylethylamine) of a premixed solution of 484 g (4 mol) of R-(+)-phenylethylamine with an enantiomer excess of 97.2% and 9.9 g (0.1 mol) of n-butyl isocyanate in 2000 g of chlorobenzene and, on average, 40.8 g/h of phosgene (corresponding to 0.41 mol/h) were introduced in parallel continuously at a temperature of 70–75° C. into the main reactor which was filled with a solution of 73.6 g of R-(+)-phenylethyl isocyanate (0.5 mol; prepared as in Examples 1–2) and 2.48 g (0.025 mol) of n-butyl isocyanate in 250 g of chlorobenzene. The after-reactor was heated to a constant temperature of 50° C. within a temperature range of 80–85° C., the stripping column, into which excess phosgene was continuously stripped out. A total of 2139 g of product was obtained. The content of R-(+)-phenylethyl isocyanate in the reaction product was determined by gas chromatography, and was 19.7 GC area %, or 90 area % (excluding solvent). 363 g of R-(+)-phenylethyl isocyanate having a purity of >98% and an enantiomer excess of 95.7% were obtained therefrom by fractional distillation. A further 60 g having a content of 45% of R-(+)-phenylethyl isocyanate remained in the reboiler.

Example 4

Isophorone Diisocyanate 4.9 g of n-butyl isocyanate (0.05 mol) and 111 g (0.5 mol) of isophorone diisocyanate were introduced into 300 g of chlorobenzene and heated to 100° C. Over the course of 15 minutes, 25 g of phosgene were passed in, and phosgene reflux occurred. Over the course of 2 h, a further 91 g of phosgene and 85.2 g (0.5 mol) of isophoronediamine (3-(aminomethyl)-3,5,5-trimethylcyclohexylamine), dissolved in 200 g of chlorobenzene, were metered in parallel at 94–98° C. After an after-reaction of 4 h at 111–113° C., excess phosgene was driven out by stripping with nitrogen at 40° C. The crude product of 645 g comprised, according to the gas chromatograph, 23 area % of isophorone diisocyanate. A total of 168 g of isophorone diisocyanate was isolated by fractional distillation under reduced pressure (1.5 mbar, 120–128° C.).

Example 5

Cyclohexyl Isocyanate 2.4 g (0.025 mol) of n-butyl isocyanate were introduced into 500 g of chlorobenzene in a phosgenation apparatus with a downstream battery of high-efficiency condensers. 40 g of phosgene (0.4 mol) were introduced, and the solution was heated to 78° C. Over the course of 140 minutes, 99.2 g (1 mol) of cyclohexylamine (dissolved in 200 g of chlorobenzene) were added dropwise, and a further 110 g (1.1 mol) of phosgene in gaseous form were introduced in parallel. The reaction temperature during the addition was maintained between 78 and 83° C. After an after-reaction time of 1 h at 87° C., excess phosgene was stripped out with nitrogen. The product of 802 g comprised, according to the gas chromatograph, 11.9 area % of cyclohexyl isocyanate. Fractional distillation under reduced pressure gave 98 g (78% of theory) of cyclohexyl isocyanate.

Example 6

Phenyl Isocyanate 2.4 g (0.025 mol) of n-butyl isocyanate were introduced into 500 g of chlorobenzene in a phosgenation apparatus with a downstream battery of high-efficiency condensers. 40 g of phosgene (0.4 mol) were introduced, and the solution was heated to 81° C. Over the course of 140 minutes, 93.1 g (1 mol) of aniline (dissolved in 200 g of chlorobenzene) were added dropwise, and a further 110 g (1.1 mol) of phosgene in gaseous form were introduced in parallel. The reaction temperature during the addition was maintained between 81 and 86° C. After an after-reaction time of 1 h at 88° C., the excess phosgene was stripped out with nitrogen. The product of 811 g comprised, according to the gas chromatograph, 12.4 area % of phenyl isocyanate. Fractional distillation under reduced pressure gave 91 g (76% of theory) of phenyl isocyanate.

Comparative Example 1

4.8 g of n-butyl isocyanate (0.05 mol) were introduced into 400 g 10 of chlorobenzene in a phosgenation apparatus with a downstream battery of high-efficiency condensers. A total of 60.5 g of R-(+)-phenylethylamine (0.5 mol) was added dropwise at room temperature over the course of 10 minutes. The batch was then heated to 70° C. At 80–86° C., a total of 61 g (0.61 mol) of phosgene was introduced over the course of 65 minutes. After 13 g of phosgene had been introduced, crystals started to form, and after 27 g of phosgene had been introduced a viscous suspension had formed, which dissolved again only slowly after the total amount of phosgene had been introduced. After an after-reaction of 2 h 30 minutes at 80° C., the excess phosgene was stripped out at 40° C. with nitrogen. The reaction product of 467 g comprised, according to gas chromatographic analysis, 63.4 area % (without solvent) of R-(+)-phenylethyl isocyanate and 17.1% of higher-boiling components.

Comparative Example 1 exhibits a significantly poorer yield and reduced selectivity compared to Examples 1 and 2 according to the invention. In addition, the formation of a suspension is observed.

Comparative Example 2

Cold-hot Phosgenation 330 g of phosgene were condensed into 1000 g of chlorobenzene over the course of 130 minutes at −5 to +5° C. in a phosgenation apparatus with a downstream battery of high-efficiency condensers.

181.5 g of R-phenylethylamine (1.5 mol, dissolved in 750 g of chlorobenzene) were added dropwise over 50 minutes. A thick suspension formed which was just still stirrable. After all of the amine had been added, the mixture was heated at 59° C. over the course of 1 h. Phosgene reflux occurred. The batch was stirred for 90 minutes at 59–68° C., and the solution became completely clear. The batch was stirred for a further 3.5 h at 68–86° C. The mixture was then heated at 129° C. under nitrogen over the course of 2.5 h. At 125–130° C., a further 30 g of phosgene were introduced, and the mixture was stirred for 2 h under reflux at 126° C. With cooling to 50° C., excess phosgene was stripped out with nitrogen at room temperature firstly for 3.5 h and then for a further 4 h. 1600 g of chlorobenzene were distilled off from the reaction product initially at 40 mbar and 43–44° C. The residue was fractionally distilled over a 30 cm column (filled with 5 mm glass rings). The main fraction passed over at 7 mbar and 74–75° C. A total of 179 g (corresponds to 81% of theory) of R-(+)-phenylethyl isocyanate having a purity of 98.5% was isolated.

The Comparative Example illustrates the disadvantages of the customary cold-hot phosgenation, namely long reaction times, the formation of a suspension which is difficult to handle on an industrial scale, and the low concentration of the amine/isocyanate in the solution (final concentration of isocyanate about 11% by weight). As Examples 1 and 2 show, the process according to the invention permits significantly higher concentrations (16–20% by weight of the amine/isocyanate in the solution). At additionally lower experimental times this means a considerable increase in the achievable space-time yield.

We claim:

1. A process for the preparation of aliphatic, cycloaliphatic, araliphatic and aromatic mono- and oligo-isocyanates by phosgenation of the corresponding primary amines at atmospheric pressure, which comprises a) introducing a catalytic amount of a monoisocyanate (isocyanate a) into an inert solvent together with phosgene;

b) adding the primary amine, and c) reacting the resulting reaction mixture with phosgene.

2. A process as claimed in claim 1, which is carried out at from 50 to 120° C.

3. A process as claimed in claim 1, wherein the reaction is carried out in o-, m-, p-xylene, chlorobenzene, dichlorobenzenes or mixtures thereof.

4. A process as claimed in claim 1, wherein the isocyanate a is used in an amount of from 0.01 to 25 mol %, based on the primary amine.

5. A process as claimed in claim 1, wherein the isocyanate a used is a linear, aliphatic $C_3$- to $C_{10}$-monoalkyl isocyanate.

6. A process as claimed in claim 1, wherein the primary amine used is an aliphatic $C_3$- to $C_{30}$-alkylamine, a cycloaliphatic $C_3$- to $C_{20}$-cycloalkylamine, an araliphatic amine having from 7 to 12 carbon atoms or a $C_4$- to $C_{10}$-arylamine.

7. A process as claimed in claim 1, wherein the primary amine used is hexamethylenediamine, cyclohexylamine, isophoronediamine, toluylenediamine, aniline, R-(+)- or S-(−)-phenylethylamine.

* * * * *

UNITED STATES PATENT AND TRADEMARK OFFICE
CERTIFICATE OF CORRECTION

PATENT NO. : 6,683,204 B1
DATED : January 27, 2004
INVENTOR(S) : Stamm et al.

It is certified that error appears in the above-identified patent and that said Letters Patent is hereby corrected as shown below:

<u>Title page,</u>
Item [86], PCT No.:, "Mar. 4, 2000" should be -- Mar. 4, 2002 --.

Signed and Sealed this

Fifteenth Day of June, 2004

JON W. DUDAS
*Acting Director of the United States Patent and Trademark Office*